(12) United States Patent
Reeves et al.

(10) Patent No.: US 6,312,891 B1
(45) Date of Patent: *Nov. 6, 2001

(54) **SPECIES-SPECIFIC DNA PROBES FOR *VIBRIO VULNIFICUS* AND *VIBRIO CHOLERAE*, METHODS AND KITS**

(75) Inventors: Robert H. Reeves; Brenda W. Bennison, both of Tallahassee, FL (US); Paul A. LaRock, Baton Rouge, LA (US)

(73) Assignee: Florida State University, Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/843,119

(22) Filed: Apr. 21, 1997

Related U.S. Application Data

(60) Continuation of application No. 08/474,828, filed on Jun. 7, 1995, now abandoned, which is a division of application No. 07/891,987, filed on May 28, 1992, now Pat. No. 5,426,025.

(51) Int. Cl.$^7$ ............................... C12Q 1/68; C07H 21/04
(52) U.S. Cl. ....................... 435/6; 435/252.1; 536/24.32; 536/24.33
(58) Field of Search ................. 435/6, 252.1; 536/24.32, 536/24.33

(56) References Cited

U.S. PATENT DOCUMENTS

| | | | |
|---|---|---|---|
| 4,582,789 | * 4/1986 | Sheldon, III et al. | 435/6 |
| 5,258,284 | * 11/1993 | Morris, Jr. et al. | 435/6 |
| 5,582,993 | * 12/1996 | Stackebrandt et al. | 435/6 |
| 5,607,835 | * 3/1997 | Reeves et al. | 435/6 |

FOREIGN PATENT DOCUMENTS

| | | |
|---|---|---|
| 5137600 | * 6/1993 | (JP) . |
| 5276996 | * 10/1993 | (JP) . |
| 8803957 | * 6/1988 | (WO) . |

OTHER PUBLICATIONS

Dorsch et al., *Int. J. Syst. Bacteriol.* 42(1), 58–63 (Jan. 1992).*
Aznar et al.,*Int. J. Syst. Bacteriol.* 44(2), 330–337 (1994).*
Ruimy et al., Int. J. Syst. Bacteriol. 44(3), 416–426 (1994).*
Betzl et al., *Applied Environ. Micro.* 56(9), 2927–2929 (1990).*
Amann et al.: *J. Bacteriol.*, 172:762–770 (Feb. 1990).
Amann et al.: *Nature*, 351:161–164 (May 9, 1991).
Tamplin et al.: *Appl. & Environ. Microbiol.*, 57(4):1235–1240 (Apr. 1991).
Ratner: *Bio/Technology*, 6:1369–1370 (Dec. 1988).
DeLong et al.: *Research*, 28:41–44 (May 1990).
Reeves et al.: Rapid Detection of *Vibrio vulnifucus* Using a Fluorescent rDNA Probe, ASM General Meeting, New Orleans, LA, May 1992 (Abstract).
Amann, R.I. et al.: Flourescent–Oligonucleotide Probing of Whole Cells for Determinative, Phylogenetic and Environmental Studies in Microbiology, *J. of Bacteriology*, 172:762–770 (Feb. 1990).
Amann, R. et al.: Identification In Situ and Phylogeny of Uncultured Bacterial Endosymboints, *Nature*, 351:161–164 (May 9, 1991).
Tamplin, M.L. et al.: Enzyme Immunoassay for Identification of *Vibrio vulnificus* in Seawater, Sediment, and Oysters, *Applied and Environmental Microbiology*, 57(4):1235–1240 (Apr. 1991).
Ratner, M.: DNA Probes: The Marekt Versus the Magic, *Bio/Technology*, 6:1369–1370 (Dec. 1988).
DeLong, E.F. et al.: Fluorescent, Ribosomal RNA Probes for Clinic Application: A Research Review, *Research*, 28:41–44 (May 1990).

* cited by examiner

*Primary Examiner*—Kenneth R. Horlick
(74) *Attorney, Agent, or Firm*—Akerman, Senterfitt & Eidson

(57) ABSTRACT

The present invention relates to species-specific DNA probes specific for *Vibrio vulnificus* and *Vibrio cholerae*. The DNA probes of the present invention specifically detects *Vibrio vulnificus* or *Vibrio cholerae* in a mixed bacterial sample based on unique ribosomal RNA nucleotide sequences. When the DNA probes of the present invention are tagged with a labeled molecule such as a fluorescent label, it affords direct and immediate visualization of individual bacterial cells, and a rapid method of detection of bacterial infection in humans and shellfish without culturing.

36 Claims, No Drawings

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CGCTTCATTG AGCTA                        15

(2) INFORMATION FOR SEQ ID NO:2:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

CGCTTCATTG AGCTAT                      16

(2) INFORMATION FOR SEQ ID NO:3:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

CGCTTCATTG AGCTATG                                                      17

(2) INFORMATION FOR SEQ ID NO:4:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

CGCTTCATTG AGCTATGT                                                     18

(2) INFORMATION FOR SEQ ID NO:5:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

TGGCTTCATT GAGCTA                                                       16

(2) INFORMATION FOR SEQ ID NO:6:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

TGGCTTCATT GAGCTAT                                                      17

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

TGGCTTCATT GAGCTATG                                                     18

(2) INFORMATION FOR SEQ ID NO:8:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

TGGCTTCATT GAGCTATGT                                                    19

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TTCGCTTCAT TGAGCTAT                                                      18

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TTCGCTTCAT TGAGCTATG                                                     19

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TTCGCTTCAT TGAGCTATGT                                                    20

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GATTCCTAGG TTGAGCCCA                                                     19

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GATTCCTAGG TTGAGCCCAG                                                    20

SPECIES-SPECIFIC DNA PROBES FOR *VIBRIO VULNIFICUS* AND *VIBRIO CHOLERAE*, METHODS AND KITS

This is a continuation of application Ser. No. 08/474,828 filed on Jun. 7, 1995 abandoned, which is a division of Ser. No. 07/891,987, filed May 28, 1992, U.S. Pat. No. 5,426,025.

FIELD OF THE INVENTION

The present invention relates to species-specific oligonucleotide probes for binding specifically to ribosomal RNA of bacterium *Vibrio Vulnificus* or *Vibrio cholerae*. The present invention further relates to methods and kits for identifying the bacteria *Vibrio vulnificus* or *Vibrio cholerae* with such probes in a single day, without the need for culturing the bacteria.

BACKGROUND OF THE INVENTION

*Vibrio vulnificus* and *Vibrio cholerae* are small organisms called bacteria that live in the marine environment. *Vibrio cholerae* can also survive in fresh water. By drinking water, eating fruits and vegetables, fish or shellfish that are contaminated with this bacterium (one bacteria), a person can become very ill or may even die from the disease cholera which causes severe diarrhea and dehydration. *Vibrio vulnificus* can cause serious illness and even death within three days in people who eat raw or improperly cooked fish or shellfish that are infected with this microorganism.

There are many types of bacteria, both good and bad, in food and water. To find out whether water or food contains these harmful Vibrio bacteria, or if a person is infected with them, laboratory tests must be performed. The first step is to culture, or grow, the bacteria in a special liquid. Then a series of tests are done to identify the bacteria based on whether or not they use certain sugars and other compounds in order to grow. It may take as long as one week to do these tests and by that time a person may die if not given the proper medicine. What is needed is a rapid and easy way to detect and identify *Vibrio cholerae* and *Vibrio vulnificus*.

A faster way to check for the presence of these bacteria is to use a molecule called an antibody that recognizes then binds to a specific part of the bacterium. See, for example, Tamplin, M. L. et al.: *Applied and Environmental Microbiology*, 57:1235–1240 (April 1991), which reports an enzyme immunoassay for the identification of *Vibrio vulnificus* in seawater, sediment and oysters. However, this method also requires growing the bacteria first and still takes several days to do. Also, antibodies may be too specific and detect only those bacteria from one source but not from another.

Another method involves the use of a "gene probe" to identify the bacteria. Every living organism has molecules of DNA (deoxyribonucleic acid) which contains instructions for each cell to make the things it needs to sustain life. A gene is a piece of DNA that instructs the cell to make one particular type of protein molecule. A gene probe is also made of DNA. See, for example, Amann, R. et al.: *Nature*. 351:161–164 (May 9, 1991); and Amann, R. et al.: *J. Bacteriology*. 173:762–770 (February 1990).

*Vibrio vulnificus* and *Vibrio cholerae* have specific genes that make proteins which are responsible for causing sickness. A gene probe that specifically seeks out the genes for these toxic proteins can be used to find out whether these bacteria are in food, water or people. However, there is a problem with using a gene probe. Bacteria are one-celled organisms. Each bacterium has only one gene for each kind of protein it makes. It is difficult to detect the one and only toxic protein gene in each cell.

One way to solve this problem is to use a method called PCR to amplify (make many copies of) the gene in a test tube and then use the gene probe to find the gene copies. This method, however, is sophisticated and time-consuming and requires a sufficient number of bacteria to perform the method.

With the current outbreak of Vibrio cholerae in South America, it is apparent that a rapid means of detection is warranted. Consequently, there is a need in the industry for simple, but quick and accurate tests for the reliable and early detection of the bacteria *Vibrio vulnificus* or *Vibrio cholerae* in, for example, water, food, blood, feces, and the like, contaminated with such bateria.

SUMMARY OF THE INVENTION

In brief, the present invention alleviates and overcomes certain of the above-referenced problems and shortcomings of the present state of the art through the discovery of novel oligonucleotide probes which are species-specific for the 23S rRNA of *Vibrio vulnificus* and *Vibrio cholerae*. Generally speaking, the DNA probes of the present invention seek out and hybridize with specific, unique RNA regions of each 23S ribosome in every cell of either the bacteria *Vibrio vulnificus* or the bacteria *Vibrio cholerae*. The probes of the present invention are uniquely made of very short pieces of DNA, so small that they can easily enter a *Vibrio vulnificus* or *Vibrio cholerae* cell, respectively.

The DNA probes of the instant invention are amazingly versatile in that they can be mixed with for example, water, food such as fish or shellfish, blood, feces or other type of samples to be tested. To identify the bacteria, a labeled moiety, such as a dye, a biotin or a radioisotope molecule, is attached to one end of each DNA probe. When a fluorescent dye is selected and a light is shone on the sample (food, water, fish, shellfish, blood, feces, etc.), the fluorescent dye will glow only if the bacteria for which the DNA probe is specific are present. Quite amazingly, it is actually possible to see each tiny bacterium glowing by using an epifluorescent microscope. And, because there is no need to culture or grow the bacteria beforehand or to amplify their genes, the tests of the present invention are simpler, much quicker and more reliable than the other kinds of test which have been available heretofore for detecting *Vibrio vulnificus* and *Vibrio cholerae*.

The methods of the present invention involve fixation of whole bacterial cells from a mixed culture sample on, for example, membrane filters or microscope slides followed by hybridization with tagged species-specific probe, and washing to remove excess or non-specifically bound probe. The presence or absence of *Vibrio vulnificus* or *Vibrio cholerae* cells is directly determined by, for example, epifluorescence microscopy when the DNA probes are labeled with a fluorescent dye.

Each probe of the instant invention is a single-stranded oligodeoxynucleotide sequence, approximately 15–20 bases in length, which specifically targets the ribosomal RNA (rRNA) component of the ribosomes within *Vibrio cholerae* or *Vibrio vulnificus* cells.

While the DNA probes of the present invention typically include between about 15 and about 20 nucleotides, it should nevertheless be understood by those skilled in this art that the present invention contemplates DNA probes of any size so long as the objectives of the present invention are not defeated, i.e., the DNA probes are of a size sufficient so that they can enter the bacteria cells, and the DNA probes include an effective number of nucleotides so that they can hybridize specifically with the ribosomal RNA of either the bacteria *Vibrio vulnificus* or the bacteria *Vibrio cholerae*, respectively.

Accordingly, it can now be appreciated that the present invention is believed to provide a valuable and worldwide solution to the *Vibrio vulnificus* and *Vibrio cholerae* art that has long sought effective and inexpensive means to quickly and reliably detect such pathogenic bacteria. As a result, the present invention can help to protect the public health, and perhaps prevent future epidemics, by its ability to detect infection in humans as well as in contaminated water and food at an early state.

The above features and advantages will be better understood with reference to the Detailed Description set out hereinbelow. It will also be understood that the biological materials of this invention are exemplary only and are not to be regarded as limitations of this invention.

DETAILED DESCRIPTION

By way of illustrating and providing a more complete appreciation of the present invention and many of the attendant advantages thereof, the following detailed description is provided concerning the novel oligonucleotide probes, methods and kits.

The DNA probes of the present invention have been developed by PCR amplification and sequencing of the genes for the 16S and 23S rRNA of *Vibrio vulnificus* and *Vibrio cholerae*. The gene sequences were then aligned with available sequences for other Vibrio and non-Vibrio rRNA genes in order to locate regions of the genes which are unique to *Vibrio vulnificus* or *Vibrio cholerae*. The DNA probes of the instant invention work by specifically binding to their complementary rRNA sequence on the ribosome to form a DNA-RNA hybrid molecule.

The *Vibrio vulnificus* DNA probe sequences include:
SEQ ID NO:1
  CGCTTCATTGAGCTA
SEQ ID NO:2
  CGCTTCATTGAGCTAT
SEQ ID NO:3
  CGCTTCATTGAGCTATG
SEQ ID NO:4
  CGCTTCATTGAGCTATGT
SEQ ID NO:5
  TGGCTTCATTGAGCTA
SEQ ID NO:6
  TGGCTTCATTGAGCTAT
SEQ ID NO:7
  TGGCTTCATTGAGCTATG
SEQ ID NO:8
  TGGCTTCATTGAGCTATGT
SEQ ID NO:9
  TTCGCTTCATTGAGCTAT
SEQ ID NO:10
  TTCGCTTCATTGAGCTATG
SEQ ID NO:11
  TTCGCTTCATTGAGCTATGT The *Vibrio cholerae* DNA probe sequences include:
SEQ ID NO:12
  GATTCCTAGGTTGAGCCCA
SEQ ID NO:13
  GATTCCTAGGTTGAGCCCAG The DNA probes of the present invention can be made in an automated DNA synthesizer. An amino linker is attached to the 5' end of the probe to allow covalent coupling of a fluorescent dye. Dye molecules that can be attached to the probes include the isothiocyanate or sulfonyl halide forms of fluorescein, a rhodamine and other fluorephores which are commercially available. Fluorescently-tagged probes are purified on a Sephadex G-25 size exclusion column followed by HPLC. At this point, the probes are ready for use.

In addition to fluorescent dyes, the probes can be labeled with, for example, a biotin, a radioisotope, or other tag molecules and the hybridization between the probe and its target rRNA molecule is detected by means other than epifluorescence microscopy.

A method for detecting and identifying *Vibrio vulnificus* or *Vibrio cholerae* using the fluorescently-tagged or labeled DNA probes involves fixation of whole bacterial cells from a mixed culture sample (food, water, etc.) on a membrane filter or glass microscope slide followed by hybridization with the appropriate fluorescently-tagged, species-specific probe, and washing to remove excess or non-specifically bound probe. The presence or absence of *Vibrio vulnificus* or *Vibrio cholerae* cells is directly determined by epifluorescence microscopy.

Samples of environmental or clinical origin (e.g. water, shellfish, blood) to be tested for the presence of these bacteria are adhered to either glass microscope slides coated with gelatin or to non-fluorescent, inorganic, 0.2 micron membrane filters and air dried. The sample is then fixed in a formaldehyde:phosphate buffered saline solution (9:1), fixative solution A, for 20 minutes. This fixation step is repeated with fresh fixative solution. (These fixation steps can be omitted if the original sample is fresh.) Next, the sample is fixed in methanol:formaldehyde (9:1), fixative solution B, for 20 minutes, rinsed briefly in distilled water and air dried.

A small volume of a hybridization solution or buffer containing the probe is added to the fixed, dried sample. The hybridization solution or buffer includes about 0.2% sodium dodecyl sulfate (SDS), sodium chloride, sodium phosphate, EDTA (SSPE) (0.9 Molar sodium chloride, 0.06 Molar sodium phosphate, 0.006 Molar EDTA), Denhardt's solution—1×, and about 4 mcg/ml of double stranded heterologous DNA salmon sperm. When slides are selected, the hybridization solution or buffer should include enough probe so that approximately 50 nanograms of probe available per smear per slide. When filters are selected, the hybridization solution or buffer should include enough probe so that approximately 15 nanograms of probe is available per filter. The slides/filters are incubated in the dark at a specific temperature for about one to about two hours to allow hybridization between the probes and target rRNA. The hybridization temperature for the Vibrio vulnificus probe is about 51° C. The hybridization temperature for the *Vibrio cholerae* probe is about 57° C.

Washes to remove excess or non-specifically bound probes are performed at room temperature for a total of about 12 minutes followed by about a 20 minute wash at the hybridization temperature with a solution of lower salt content (wash solution B) than that of the first wash solution (wash solution A). Wash solution A includes 0.2% SDS and 6×SSPE (0.9 Molar sodium chloride, 0.06 Molar sodium phosphate, and 0.006 Molar EDTA). Wash solution B includes 0.2% SDS and 1×SSPE (0.15 Molar sodium chloride, 0.01 Molar sodium phosphate and 0.001 Molar EDTA). Slides/filters are rinsed briefly with distilled water, air dried in the dark, and viewed with an epifluorescence microscope.

To summarize a procedure of the present invention:
1. fix cells about (20–60 minutes);
2. hybridize with fluorescently-labeled probe solution (about 1–2 hours);
3. Wash to remove non-specifically bound probe (about 35 minutes); and
4. view cells with epifluorescence microscope.

A typical kit of the present invention includes: fixative solutions A & B; fluorescently-labeled oligonucleotide DNA probe (5 nanograms/ml water); hybridization buffer; wash solutions A & B; and non-fluorescent filters or Teflon-coated microscope slides (with sample wells).

The DNA probes of the present invention have been laboratory tested and are believed to be species-specific. Fluorescently-tagged species-specific DNA probes of the present invention, which target rRNA, have been successfully used for both environmental research and clinical diagnostic purposes. The advantages of using such DNA probes for detecting and identifying *Vibrio vulnificus* or *Vibrio cholerae* in either environments or clinical samples include the following: 1. rapid (one day) diagnosis; 2. elimination of the need for prior culturing of the bacteria in test sample; 3. the probes are small enough to penetrate whole, intact, fixed bacterial cells (in situ hybridization); 4. elimination of the need to extract or amplify DNA; 5. detection of target organisms in a mixed bacterial sample; 6. fluorescent label allows direct and immediate visualization of individual cells; 7. fluorescently-labeled probes are stable, sensitive and safe; and 8. methods utilize standard clinical and research laboratory equipment and requires minimal technical expertise.

Applications of the probes contemplated by the present invention include, for instance, clinical usage to rapidly diagnose human infections of *Vibrio vulnificus* or *Vibrio cholerae*, regulatory agency use to detect bacteria in water and food (especially important in oyster meat), and research usage for ecological studies of the seasonality and distribution of these bacteria in the environment.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

Having described our invention, we claim:

1. An oligonucleotide probe specific for *Vibrio vulnificus*, said oligonucleotide probe being capable of hybridizing specifically with a ribosomal RNA sequence selected from the group consisting of:
    CGCTTCATTGAGCTA (SEQ ID NO:1)
    CGCTTCATTGAGCTAT (SEQ ID NO:2)
    CGCTTCATTGAGCTATG (SEQ ID NO:3)
    CGCTTCATTGAGCTATGT (SEQ ID NO:4)
    TGGCTTCATTGAGCTA (SEQ ID NO:5)
    TGGCTTCATTGAGCTAT (SEQ ID NO:6)
    TGGCTTCATTGAGCTATG (SEQ ID NO:7)
    TGGCTTCATTGAGCTATGT (SEQ ID NO:8)
    TTCGCTTCATTGAGCTAT (SEQ ID NO:9)
    TTCGCTTCATTGAGCTATG (SEQ ID NO:10)
    TTCGCTTCATTGAGCTATGT (SEQ ID NO:11); and
    complementary sequences thereto.

2. An oligonucleotide probe as recited in claim 1, said probe further including a label.

3. An oligonucleotide probe as recited in claim 2, said label being a fluorophore.

4. An oligonucleotide probe as recited in claim 3, said fluorophore being selected from the group consisting of a fluoroscein isothiocyanate, a fluoroscein sulfonyl halide and a rhodamine.

5. An oligonucleotide probe as recited in claim 2, said label being selected from the group consisting of biotin and a radioisotope.

6. A method of identifying a *Vibrio vulnificus*, said method comprising:
    hybridizing the labeled probe of claim 2 to ribosomal RNA of the *Vibrio vulnificus*; and
    detecting the labeled probe hybridized to the ribosomal RNA to identify the *Vibrio vulnificus*.

7. A method as recited in claim 6, said method including the further step of:
    fixing the *Vibrio vulnificus* prior to said hybridizing.

8. A method as recited in claim 7, wherein said detecting step comprises:
    detecting the hybridized labeled probe with a epifluorescence microscope.

9. An oligonucleotide probe specific for *Vibrio cholerae*, said oligonucleotide probe having an oligonucleotide sequence for hybridizing specifically with a ribosomal RNA segment, the ribosomal RNA segment comprising a nucleotide sequence selected from the group consisting of:
    GATTCCTAGGTTGAGCCCA (SEQ ID NO: 12);
    GATTCCTAGGTTGAGCCCAG (SEQ ID NO: 13); and
    complementary sequences thereto.

10. An oligonucleotide probe as recited in claim 9, said probe further including a label.

11. An oligonucleotide probe as recited in claim 10, said label being a fluorophore.

12. An oligonucleotide probe as recited in claim 11, said fluorophore being selected from the group consisting of a fluoroscein isothiocyanate, a fluoroscein sulphonyl halide and a rhodamine.

13. An oligonucleotide probe as recited in claim 10, said label being selected from the group consisting of biotin and a radioisotope.

14. A method of identifying a *Vibrio cholerae*, said method comprising:
    hybridizing the labeled probe of claim 10 to ribosomal RNA of the *Vibrio cholerae*; and
    detecting the labeled probe hybridized to the ribosomal RNA to identify the *Vibrio cholerae*.

15. A method as recited in claim 14, said method including the further step of:
    fixing the *Vibrio cholerae* prior to said hybridizing.

16. A method as recited in claim 14, wherein said detecting step comprises:
    detecting the hybridized labeled probe with an epifluorescence microscope.

17. An oligonucleotide probe specific for a *Vibrio vulnificus* bacterium, said oligonucleotide probe having a sequence selected from the group consisting of:
    CGCTTCATTGAGCTA (SEQ ID NO:1)
    CGCTTCATTGAGCTAT (SEQ ID NO:2)
    CGCTTCATTGAGCTATG (SEQ ID NO:3)
    CGCTTCATTGAGCTATGT (SEQ ID NO:4)
    TGGCTTCATTGAGCTA (SEQ ID NO:5)
    TGGCTTCATTGAGCTAT (SEQ ID NO:6)
    TGGCTTCATTGAGCTATG (SEQ ID NO:7)
    TGGCTTCATTGAGCTATGT (SEQ ID NO:8)
    TTCGCTTCATTGAGCTAT (SEQ ID NO:9)
    TTCGCTTCATTGAGCTATG (SEQ ID NO:10)
    TTCGCTTCATTGAGCTATGT (SEQ ID NO:11); and
    complementary sequences thereto.

18. An oligonucleotide probe as recited in claim 17, said oligonucleotide probe further including a label.

19. An oligonucleotide probe as recited in claim 18, said label being a fluorophore.

20. An oligonucleotide probe as recited in claim 19, said fluorophore being selected from the group consisting of a fluoroscein isothiocyanate, a fluoroscein sulfonyl halide and a rhodamine.

21. An oligonucleotide probe as recited in claim 18, said label being selected from the group consisting of biotin and a radioisotope.

22. A method of identifying a *Vibrio vulnificus* bacterium, said method comprising:
    hybridizing the labeled probe of claim 18 to a region of the 23S ribosomal RNA of the *Vibrio vulnificus* bacterium; and
    detecting the labeled probe hybridized to the 23S ribosomal RNA to identify the *Vibrio vulnificus* bacterium as a *Vibrio vulnificus* bacterium.

23. A method as recited in claim 22, said method including the further step of fixing a *Vibrio vulnificus* bacterium prior to said hybridizing.

24. A method as recited in claim 23, wherein said detecting step comprises detecting the hybridized labeled probe with an epifluorescence microscope.

25. A fixed *Vibrio vulnificus* bacterium having hybridized thereto an oligonucleotide probe specific for a region of the 23S ribosomal RNA of said *Vibrio vulnificus* bacterium, wherein the oligonucleotide probe comprises a label, and wherein the region of the 23S ribosomal RNA comprises a sequence selected from the group consisting of:
    CGCTTCATTGAGCTA (SEQ ID NO:1)
    CGCTTCATTGAGCTAT (SEQ ID NO:2)
    CGCTTCATTGAGCTATG (SEQ ID NO:3)
    CGCTTCATTGAGCTATGT (SEQ ID NO:4)
    TGGCTTCATTGAGCTA (SEQ ID NO:5)
    TGGCTTCATTGAGCTAT (SEQ ID NO:6)
    TGGCTTCATTGAGCTATG (SEQ ID NO:7)
    TGGCTTCATTGAGCTATGT (SEQ ID NO:8)

TTCGCTTCATTGAGCTAT (SEQ ID NO:9)
TTCGCTTCATTGAGCTATG (SEQ ID NO:10)
TTCGCTTCATTGAGCTATGT (SEQ ID NO:11); and complementary sequences thereto.

26. A fixed *Vibrio vulnificus* bacterium as recited in claim 25, said label being a fluorophore.

27. A fixed *Vibrio vulnificus* bacterium as recited in claim 26, said fluorophore being selected from the group consisting of a fluoroscein isothiocyanate, a fluoroscein sulfonyl halide and a rhodamine.

28. A fixed *Vibrio vulnificus* bacterium as recited in claim 25, said label being selected from the group consisting of biotin and a radioisotope.

29. A fixed *Vibrio vulnificus* bacterium as recited in claim 25, wherein said fixed *Vibrio vulnificus bacterium is attached to a substrate selected from the group consisting of a slide and a membrane.*

30. A fixed *Vibrio cholerae* bacterium having hybridized thereto a probe with a label, said labeled probe being specific for a region of 23S ribosomal RNA of said *Vibrio cholerae* bacterium, the region of 23S ribosomal RNA comprising a sequence selected from the group consisting of:

GATTCCTAGGTTGAGCCCA (SEQ ID NO: 12);
GATTCCTAGGTTGAGCCCAG (SEQ ID NO: 13); and complementary sequences thereto.

31. A fixed *Vibrio cholerae* bacterium as recited in claim 30, said label being a fluorophore.

32. A fixed *Vibrio cholerae* bacterium as recited in claim 31, said fluorophore being selected from the group consisting of a fluoroscein isothiocyanate, a fluoroscein sulphonyl halide and a rhodamine.

33. A fixed *Vibrio cholerae* bacterium as recited in claim 30, said label being selected from the group consisting of biotin and a radioisotope.

34. A fixed *Vibrio cholerae* bacterium as recited in claim 30, wherein said *Vibrio cholerae* bacterium is fixed to a substrate selected from the group consisting of a slide and a membrane.

35. A kit for detecting a *Vibrio vulnificus* bacterium, said kit comprising:

an oligonucleotide probe as recited in claim 17, and at least one component selected from the group consisting of a fixative solution, hybridization buffer, wash solution, non-fluorescent filter, slide and membrane.

36. A kit for detecting a *Vibrio cholerae* bacterium, said kit comprising:

an oligonucleotide probe as recited in claim 10; and at least one component selected from the group consisting of a fixative solution, hybridization buffer, wash solution, non-fluorescent filter, slide and membrane.

* * * * *